US00PP27642P3

(12) United States Plant Patent
Weber

(10) Patent No.: US PP27,642 P3
(45) Date of Patent: Feb. 7, 2017

(54) ***VACCINIUM* PLANT NAMED 'WINTER BELL'**

(50) Latin Name: ***Vaccinium* spp.**
Varietal Denomination: Winter Bell

(71) Applicant: David Weber, Winter Haven, FL (US)

(72) Inventor: David Weber, Winter Haven, FL (US)

(73) Assignee: Weber Genetics, LLC, Winter Haven, FL (US)

( * ) Notice: Subject to any disclaimer, the term of this patent is extended or adjusted under 35 U.S.C. 154(b) by 172 days.

(21) Appl. No.: 14/121,437

(22) Filed: Sep. 8, 2014

(65) Prior Publication Data

US 2016/0073561 P1 Mar. 10, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Keith Robinson
(74) *Attorney, Agent, or Firm* — Cassandra Bright

(57) ABSTRACT

A new and distinct *Vaccinium* spp. cultivar named 'WINTER BELL' is disclosed, characterized by a semi-upright plant habit, vigorous growth and semi-deciduous habit in Florida. The new variety shows tolerance for wetter soil conditions. Fruit yield is exceptionally high, with fruit ripening early, with first harvest in mid to late March. Fruit is somewhat bell-shaped with good size and an attractive waxy coating. The new variety is a *Vaccinium*, and is normally used as an ornamental garden or landscape plant.

5 Drawing Sheets

Latin name of the genus and species: *Vaccinium* spp.
Variety denomination: 'WINTER BELL'.

BACKGROUND OF THE INVENTION

The new cultivar was discovered as the product of a breeding program conducted in Winter Haven, Fla., by the breeder David Weber. 'Winter Bell' was selected from open pollinated seedlings of the undistributed, unpatented variety referred to by code FL 95-174 which were planted in Winter Haven, Fla. in June, 2008. The pollen parent is unknown. Due to its earliness and fruit quality 'Winter Bell' was selected for yield evaluation in 2012. 'Winter Bell' was evaluated as a single plant test against other commercial varieties in 2012 and 2013 and planted in a confidential, controlled field test plot in June, 2013.

'Winter Bell' has been asexually propagated over numerous generations by softwood cuttings in Winter Haven, Fla., and all propagated material has retained the vegetative and fruit characteristics of the mother plant. First asexual propagation was performed June 2012, in Winter Haven, Fla. at a commercial nursery.

Asexual reproduction of the new cultivar 'WINTER BELL' by vegetative cuttings was performed at the nursery in Hawthorne, Fla. in September of 2007. Vegetative reproduction by cuttings has produced multiple generations, and has shown that the unique features of this cultivar are stable and reproduced true to type through successive generations.

SUMMARY OF THE INVENTION

The cultivar 'WINTER BELL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WINTER BELL'. These characteristics in combination distinguish 'WINTER BELL' as a new and distinct *Vaccinium* spp. cultivar:

1. Exceptionally high fruit yield.
2. Early fruit ripening, first harvest in mid to late March.
3. Vigorous growth in native spodic soils.
4. Excellent fruit bloom (attractive waxy coating).
5. Excellent fruit size.
6. Excellent fruit scar.
7. Resistance to common root diseases, tolerating wetter soils.
8. Semi-evergreen to evergreen habit under Florida conditions.
9. Slight bell shape to fruit.
10. Semi-upright habit.
11. Fruit of average firmness.

PARENT COMPARISON

Plants of the new cultivar 'WINTER BELL' are similar to plants of the parent variety in most horticultural characteristics. However, plants of the new cultivar 'WINTER BELL' differ from FL 95-174 in the following:

1. 'Winter Bell' has larger leaves.
2. 'Winter Bell' produces larger fruit.
3. Plants of 'Winter Bell' are more upright with less lateral branching.
4. Plants of 'Winter Bell' grow more vigorously.
5. Fruit of 'Winter Bell' has a different shape.
6. Fruit occurs in loose clusters on 'Winter Bell', whereas fruit occurs on the parent variety more singularly along stem internodes.
7. Fruit pedicels of 'Winter Bell' are longer.

The pollen parent is unknown.

COMMERCIAL COMPARISON

'WINTER BELL' can be compared to the commercial variety *Vaccinium* 'Jewel' U.S. Plant Pat. No. 11,807. Plants of the new variety are similar to 'Jewel' in most horticultural characteristics, however, 'WINTER BELL' differs in the following:

1. Earlier ripening than Jewel. In testing conducted during 2012, by March 20, 'Winter Bell' produced 2.9 pounds of fruit whereas 'Jewel' produced had produced 0.28 pounds of fruit.
2. Plants of 'Winter Bell' are grow more vigorously.
3. Highly waxy leaves of 'Winter Bell' are more durable to physical stress.
4. Plants of 'Winter Bell' yield more fruit.
5. Fruit of 'Winter Bell' has a different shape.
6. Leaves are more persistent and rust resistant than foliage of 'Jewel'.

'WINTER BELL' can be compared to the commercial variety *Vaccinium* 'Emerald' U.S. Plant Pat. No. 12,165. Plants of the new variety are similar to 'Emerald' in most horticultural characteristics, however, 'WINTER BELL' differs in the following:

1. Earlier ripening than 'Emerald'. In testing conducted during 2012, by March 20, Winter Bell produced 2.9 pounds of fruit whereas 'Emerald' had no ripe fruit on this date. The subsequent measurement, March 27, resulted in 4.7 pounds total harvested to date from 'Winter Bell' and 2.9 pounds harvested to date from 'Emerald'.
2. Plant habit of 'Winter Bell' is more upright.
3. Plants of 'Winter Bell' are more tolerant of wet soils.
4. Leaves of 'Winter Bell' are more waxy.
5. Stronger waxy coating of fruit, giving an attractive, cloudier blue coloration.

BRIEF DESCRIPTION OF THE PHOTOGRAPHS

The accompanying photograph illustrate the following:

Figure 1:
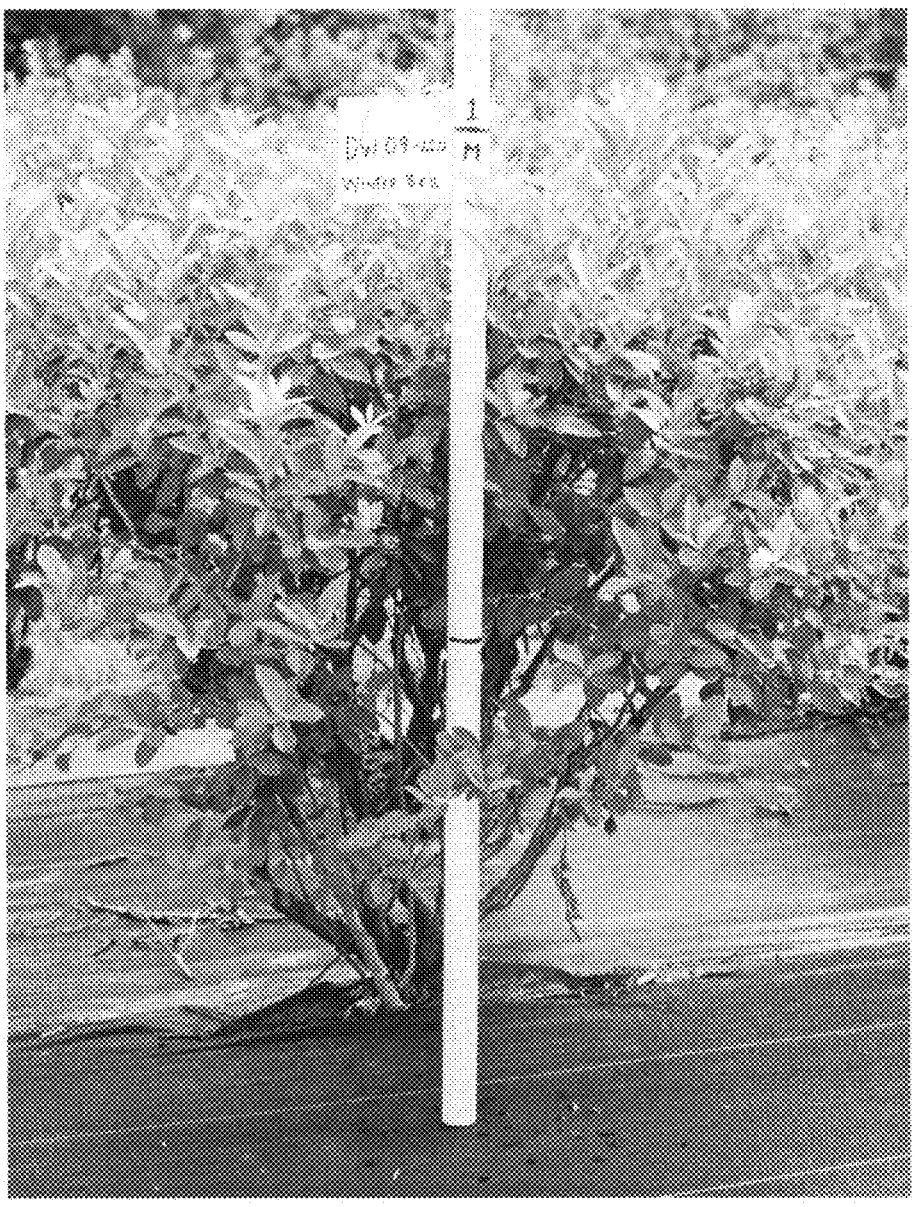
FIG. 1 illustrates in full color a typical plant of 'WINTER BELL' grown outdoors in Winter Haven, Fla. This plant is approximately 9 months old.
Figure 2:
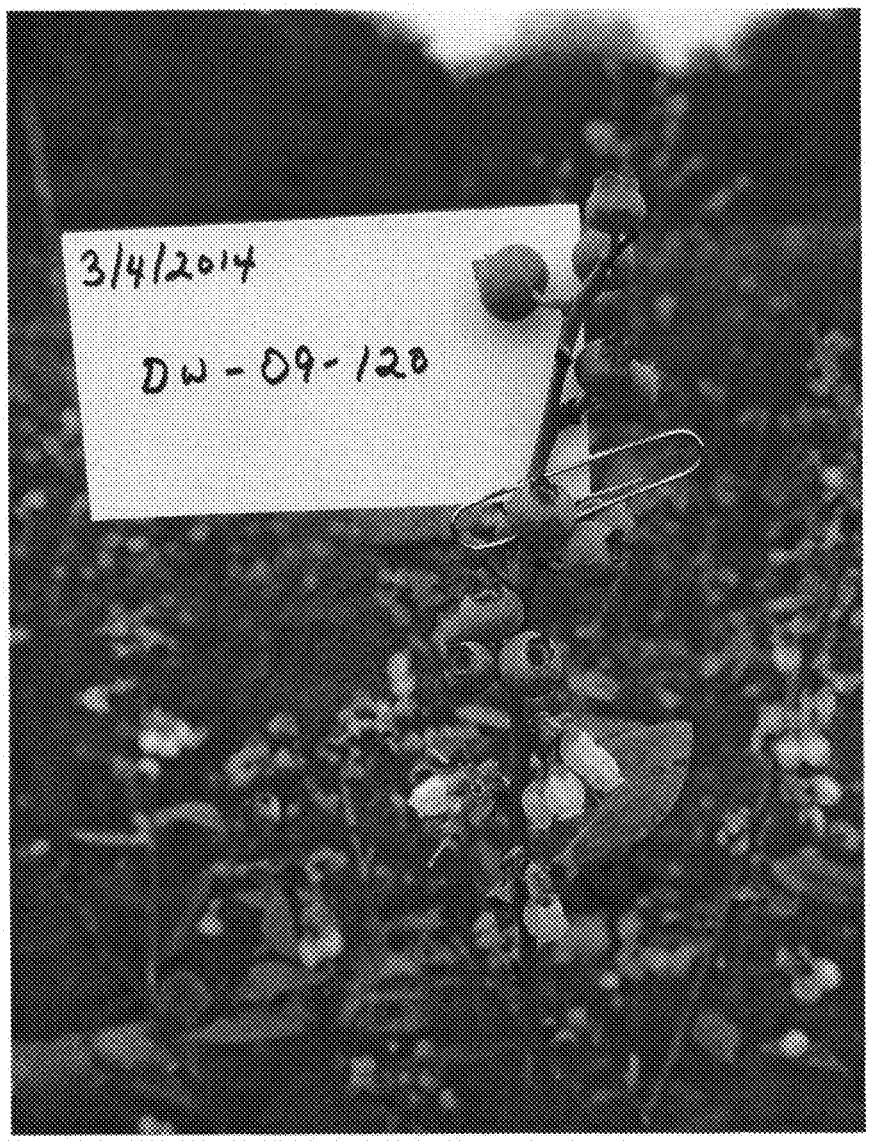
FIG. 2 illustrates in full color typical immature fruit and mature flowers of 'Winter Bell'.
Figure 3:
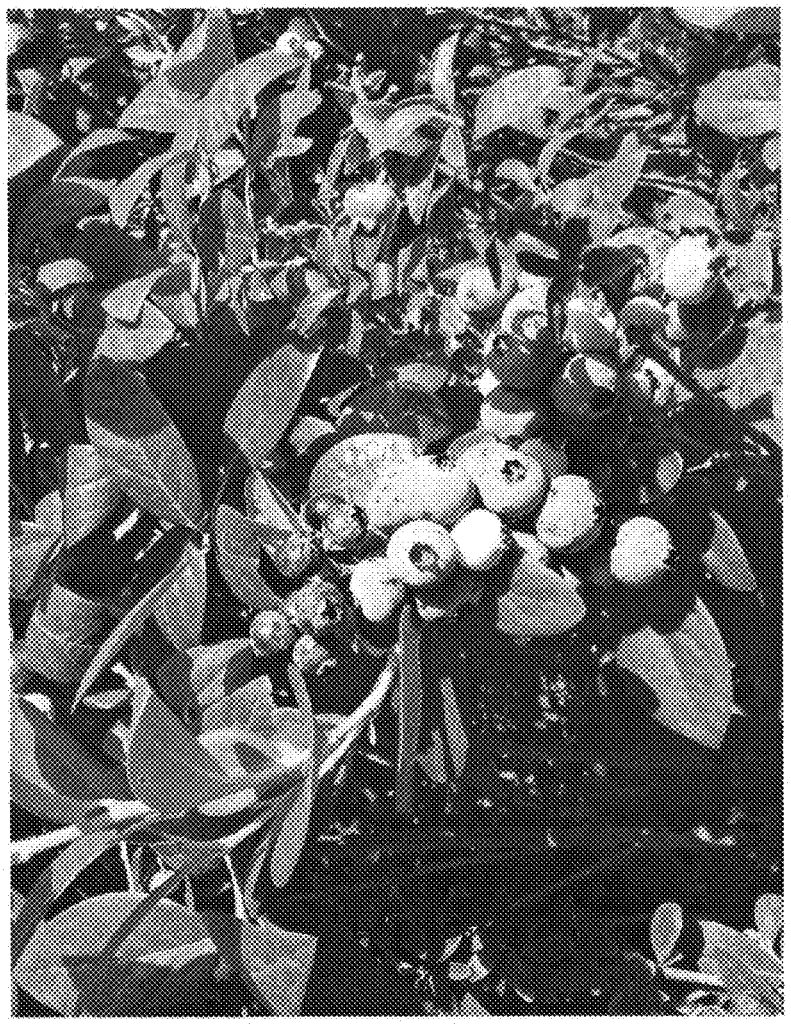
FIG. 3 illustrates in full color typical mature and immature fruit on a plant of 'WINTER BELL'.
Figure 4:
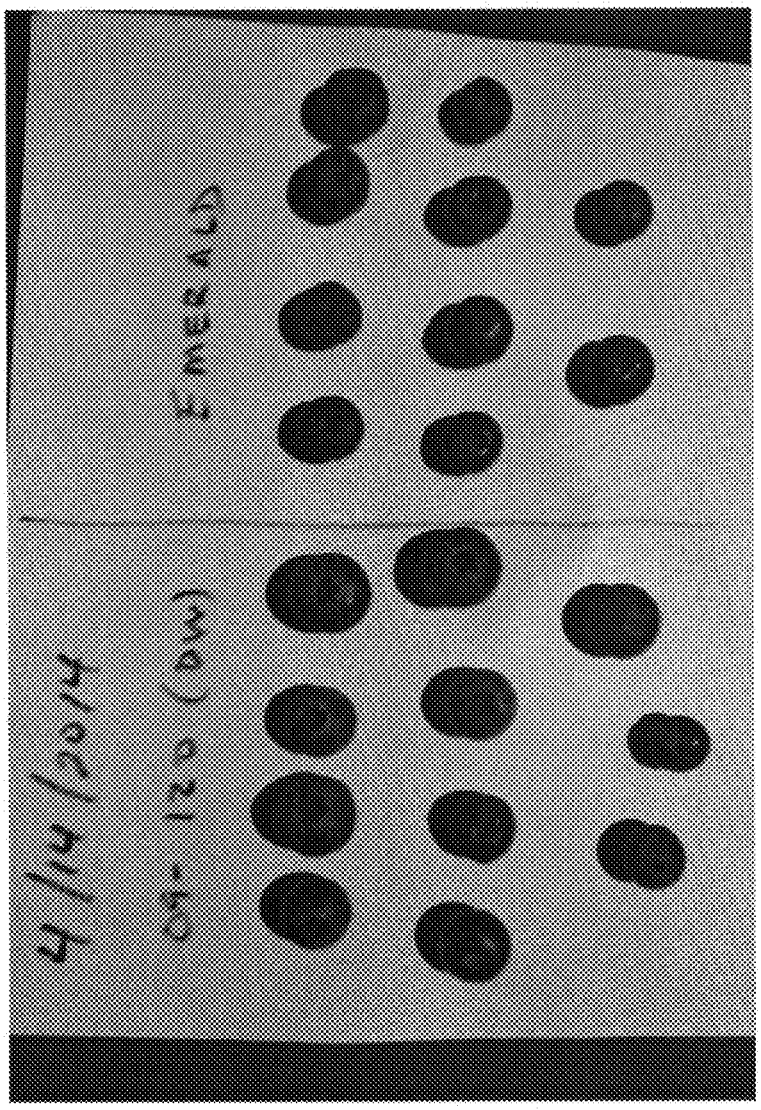
FIG. 4 illustrates in hill color typical fruits of 'WINTER BELL', referred to in the photo by the breeder code 09-120 (DW) and typical fruits of 'Emerald'.
Figure 5:
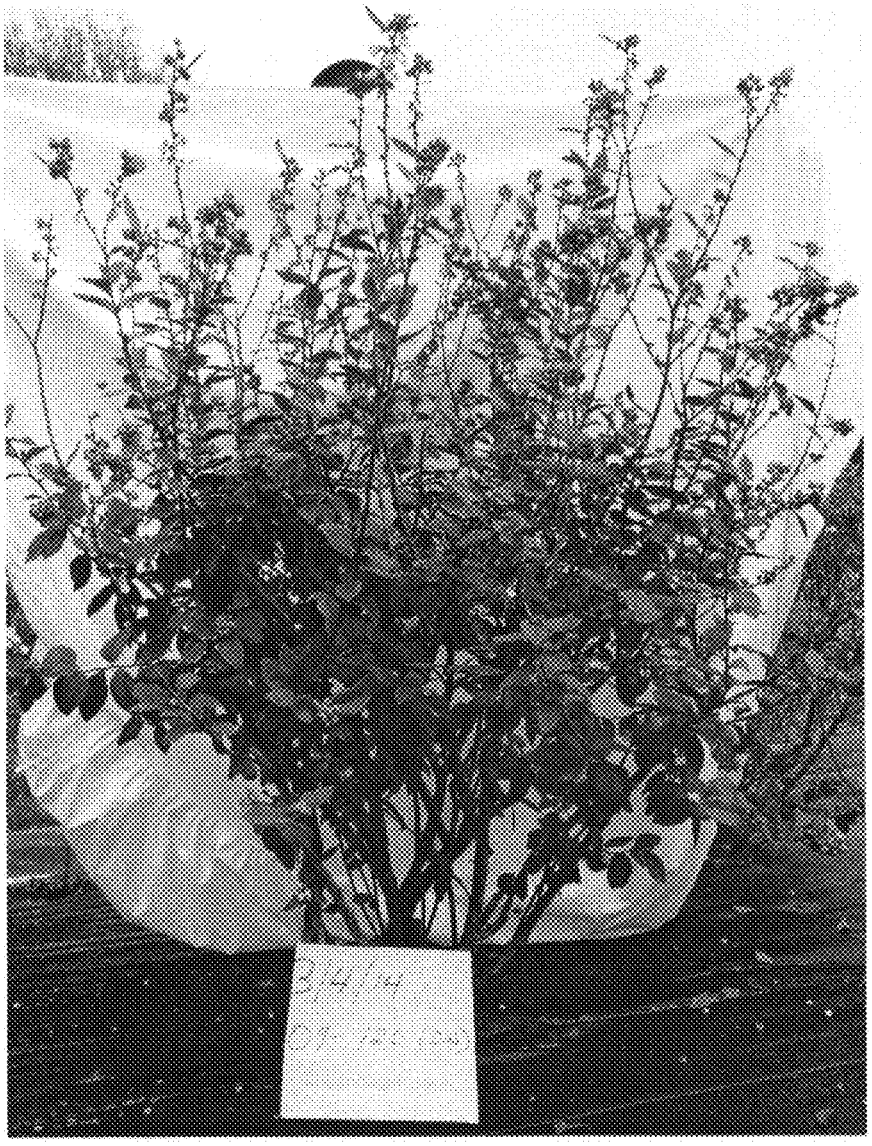
FIG. 5 illustrates in full color a typical mature plant of 'WINTER BELL' with immature fruit set.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'WINTER BELL' plants grown outdoors in Winter Haven, Fla. Year round temperature ranged from approximately 60° to 90° F., during the day and 50° to 70° F., at night with naturally high light conditions. Measurements and numerical values represent averages of typical flowering types. No chemical or photoperiodic treatments were given.

Botanical classification: *Vaccinium* spp. 'WINTER BELL'.

Age of plant described: Approximately 9 months old, planted the ground.

PROPAGATION

Typically from semi-hardwood juvenile cuttings.

Time to rooting: typically 6 to 8 weeks at 68 to 73 deg. F.

Time to produce a rooted plantlet: Approximately 3 to 4 months.

Rooting habit: Woody to semi-woody. Moderately well branched, colored near Brown 200B.

PLANT

Growth habit: Upright, semi-deciduous woody perennial shrub.

Height: Approximately 1 meter.

Plant spread: Approximately 70 cm.

Growth rate: Vigorous.

Branching characteristics: Free branching.

Texture of lateral branches: Smooth.

Color of lateral branches: Near RHS Green 143C.

Aspect: Straight, occurring at approximately 15 to 45 degree angles.

Strength of lateral branches: Very strong, very flexible.

Vegetative bud burst: Spring, typically April or May in Southern United States.

FOLIAGE

Leaf:

*Arrangement*.—Alternate.

*Average length*.—Approximately 7 cm.

*Average width*.—Approximately 4 cm.

*Shape of blade*.—Broad elliptic.

*Apex*.—Acute.

*Base*.—Obtuse.

*Attachment*.—Stalked.

*Margin*.—Entire.

*Texture of top surface*.—Highly waxy, glabrous.

*Texture of bottom surface*.—Highly waxy, glabrous.

*Leaf internode length*.—Approximate range 0.9 cm to 1.5 cm.

*Color*.—Young foliage upper side: Near RHS Green 138A. Young foliage under side: Near RHS Green 138C. Mature foliage upper side: Near RHS Green 137A, but much darker. Mature foliage under side: Near RHS Green 138B.

*Venation*.—Type: Pinnate. Venation color upperside: Near RHS Green 143B. Venation color underside: Near RHS Green 143A.

*Petiole*.—Length: Approximately 0.2 cm. Diameter: Approximately 0.2 cm. Texture: Smooth. Color upperside: Near RHS Yellow-Green 144C. Color underside: Near RHS Green 143B.

FLOWER

Natural flowering season: 50% bloom open on Feb. 15, 2014, in Winter Haven, Fla.

Inflorescence and flower type and habit: Urceolate flowers arrange in small, alternating racemes.

Quantity of flowers per raceme: Approximately 4 to 15 flowers per raceme, variable.
Diameter of raceme: Average approximately 4 to 9 cm.
Depth of raceme: Average approximately 5 to 12 cm.
Fragrance: Not observed.
Bud:
*Shape*.—Obovate.
*Length*.—Approximately 1.0 cm.
*Diameter*.—Approximately 0.8 cm.
*Color*.—Near RHS Yellow-White 158A.
Flower size:
*Diameter*.—Approximately 0.8 cm.
*Length*.—Approximately 1.1 cm.
*Corolla tube length*.—Approximately 0.9 cm.
*Color tube width*.—Approximately 0.8 cm.
Petals/corolla:
*Quantity*.—5.
*Arrangement*.—Fused.
*Length*.—Approximately 0.8 cm.
*Width*.—Approximately 0.3 cm.
*Shape*.—Completely fused, no individual shape.
*Apex*.—Acute.
*Base*.—Fused.
*Margin*.—Entire.
*Texture, upper and lower surfaces*.—Shiny.
*Color petals and tube*.—When opening, outer surface: Near RHS Yellow-White 158D, flushed near Red-Purple 62D. When opening, inner surface: Near RHS Yellow-White 158D, flushed near Red 56C. Fully opened, outer surface: Near RHS White 155A, faintly flushed near Red 56D. Thin margin coloration near Red 53C. Fully opened, inner surface: Near RHS White 155A, faintly flushed near Red 56D.
Calyx:
*Sepal quantity*.—5.
*Arrangement*.—Fused.
*Length*.—Approximately 0.5 cm.
*Width*.—Approximately 0.2 cm.
*Shape*.—Deltoid.
*Apex*.—Acute.
*Base*.—Fused.
*Margin*.—Entire.
*Texture, upper and lower surfaces*.—Matte.
*Color*.—When opening, outer surface: Near RHS Green 138A, apex flushed near Red 54B. When opening, inner surface: Near RHS Yellow-Green 144B.
Pedicels:
*Length*.—Approximately 0.3 cm to 0.5 cm
*Diameter*.—Approximately 0.1 cm.
*Strength*.—Weak to moderate.
*Texture*.—Shiny.
*Color*.—Near RHS Green 143A, slightly flushed Greyed-Purple 186D.
Peduncles:
*Length*.—Approximately 2 cm.
*Diameter*.—Approximately 0.8 cm.
*Strength*.—Moderate.
*Texture*.—Shiny.
*Color*.—Near RHS Green 138A.

REPRODUCTIVE ORGANS

Stamens:
*Number*.—Typically 10.
*Color*.—Near RHS White 155A.
*Length*.—Approximately 0.3 cm.
*Anther color*.—Near RHS Greyed-Red 179C.
*Pollen*.—Scant pollen production observed in Southern California, colored near Greyed-Purple N187D.
Pistil:
*Number*.—1.
*Length*.—Approximately 1.2 cm.
*Style*.—Length: Approximately 0.9 cm. Color: Near RHS Yellow-Green 145B.
*Stigma*.—Shape: Narrowly conical. Color: Near RHS Yellow-Green 153D. Ovary Color: Near RHS Yellow-Green 145A.
Fruit:
*Seasonal timing*.—First fruit harvested typically mid-March in the Southern United States, including Florida and Southern California.
*Fruit cluster density*.—Moderate.
*Fruiting habit*.—Fruits on both one-year old shoots and current season's shoots.
*Color*.—Immature: First near Yellow-Green 145C, changing to Blue 100C. Fully ripe: Colored close to Blue 103A, but much darker, waxy blush coloration near Blue 106D. Ripe internal coloration: Near Yellow-Green 145D.
*Diameter*.—Average 1.4 cm.
*Length*.—Average 1.2 cm.
*Acidity*.—Low.
*Sweetness*.—Medium.

OTHER CHARACTERISTICS

Disease resistance: Higher than average resistance to normal foliar diseases normal to *Vaccinium*, have been observed in this variety. Typical foliar pathogens of Vaccinium include *Alternaria tenuissima*, and *Septoria* species. Southern high-bush types are more susceptible to *Xylella fastidiosa*. The new variety appears more resistant to these varieties of foliar pathogens. Resistance to disease found in wet soil conditions also observed. The most common disease found in poorly drained soil is *Phytophthora cinnamomi*, the new variety is likely to have resistance to this pathogen.
Pest resistance: Neither resistance nor susceptibility to the normal pests of *Vaccinium*.
Drought tolerance and temperature tolerance: Low temperature tolerance and drought tolerance have not been tested.

What is claimed is:

1. A new and distinct cultivar of *Vaccinium* plant named 'WINTER BELL' as herein illustrated and described.

* * * * *